United States Patent [19]
Xu

[11] Patent Number: 5,830,337
[45] Date of Patent: Nov. 3, 1998

[54] ELECTROCHEMICAL GAS SENSOR

[75] Inventor: Xiao Xu, Fremont, Calif.

[73] Assignee: GasTech, Inc., Newark, Calif.

[21] Appl. No.: 686,088

[22] Filed: Jul. 24, 1996

[51] Int. Cl.[6] .................................................. G01N 27/26
[52] U.S. Cl. ..................... 204/400; 204/412; 204/431; 204/415; 73/31.02
[58] Field of Search ................................ 204/400, 412, 204/415, 431, 432; 73/23.31, 23.32, 31.02

[56] References Cited

U.S. PATENT DOCUMENTS

| | | | |
|---|---|---|---|
| 3,755,125 | 8/1973 | Shaw et al. | 204/195 P |
| 3,992,267 | 11/1976 | Oswin et al. | 204/1 T |
| 4,406,770 | 9/1983 | Chan et al. | 204/406 |
| 4,591,414 | 5/1986 | Zarcomb et al. | 205/787 |
| 5,395,507 | 3/1995 | Aston et al. | 204/431 |
| 5,527,446 | 6/1996 | Kosek et al. | 205/792.5 |

FOREIGN PATENT DOCUMENTS 2292804  3/1996  United Kingdom .

OTHER PUBLICATIONS p. T247 of Aldrich catalog for 1994–1995 month unavailable.

*Primary Examiner*—T. Tung
*Assistant Examiner*—Alex Noguerola
*Attorney, Agent, or Firm*—Fish & Richardson, P.C.

[57] ABSTRACT

An electrochemical gas sensor comprising a sensing electrode, a counter electrode, an electrolyte reservoir, an upwardly extending projection disposed within the reservoir that supports the counter electrode, and a wick interposed between, and in contact with, the sensing and counter electrodes. The wick includes an overhang partially disposed in the electrolyte reservoir. The sensor may further include a reference electrode coplanar with and adjacent to the counter electrode. The sensor is accurate and sensitive, while also compact, reliable, and relatively simple to manufacture.

22 Claims, 2 Drawing Sheets

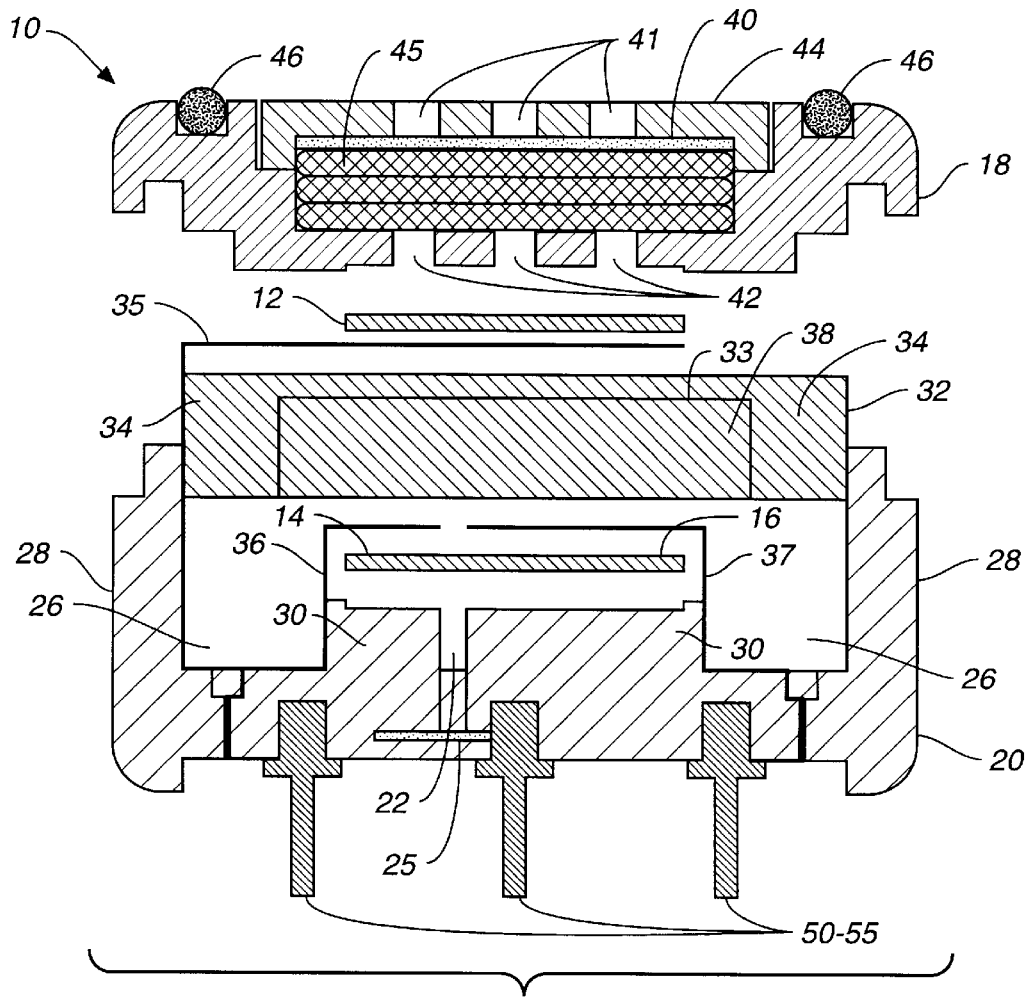
FIG._1
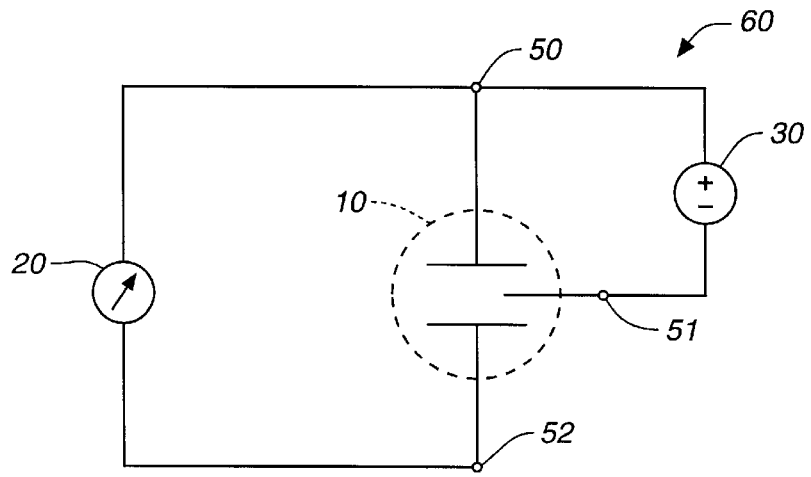
FIG._3

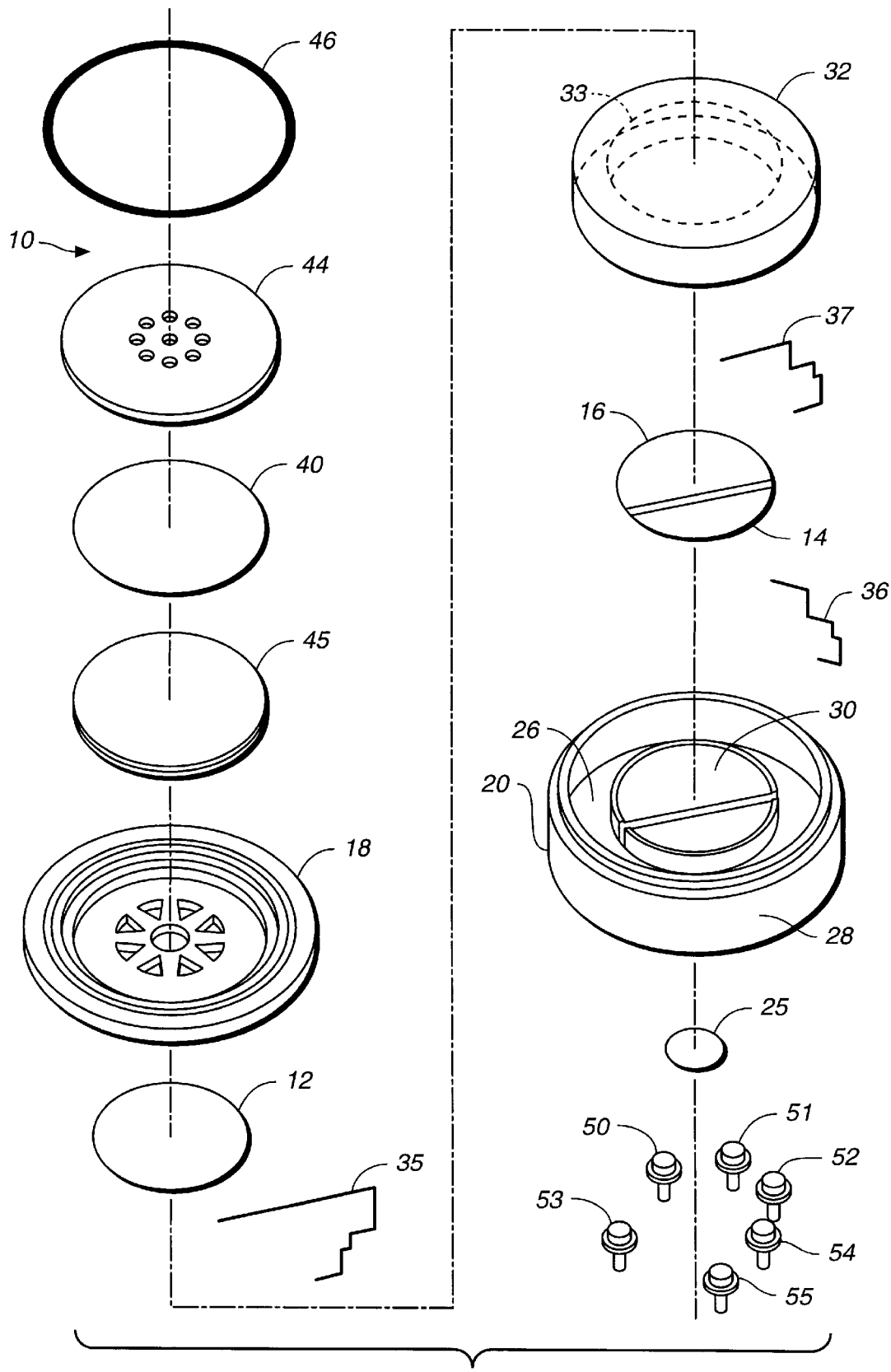
FIG._2

ELECTROCHEMICAL GAS SENSOR

BACKGROUND OF THE INVENTION

The present invention relates generally to gas sensors, and more particularly to a gas sensor utilizing an electrochemical cell that is suitable for the detection and measurement of noxious or other gases.

In recent years, great awareness has developed regarding environmental hazards that may cause explosions, fire, or toxicity. As a result, demand has arisen for instruments capable of detecting and measuring noxious gases in very low concentrations for applications such as safety monitoring and pollution control. There is a particular need for such instruments that are accurate, sensitive, compact, reliable, and relatively simple to manufacture.

Gas sensors utilizing electrochemical cells, or electrochemical gas sensors, have been used for the detection and measurement of very low concentrations of gases. Typical prior art electrochemical gas sensors include a sensing electrode, a counter electrode, and an aqueous electrolyte in contact with the electrodes. The sensor may also include a reference electrode. The sensor electrodes are made of a material that is a suitable catalyst for the gas to be detected and is a reasonable electronic conductor. The presence of a gas at the sensing electrode triggers an electrochemical reaction within the sensor. This reaction produces a current between the sensing and counter electrodes that is proportional to the concentration of the gas.

A major concern with electrochemical gas sensors is ensuring an adequate electrolyte connection between the electrodes, which is essential for the basic operation of the sensor. This connection may easily be interrupted by variations in the sensor environment, such as changes in sensor attitude or humidity. To minimize this problem, electrochemical gas sensors use wicks and/or separators to convey the aqueous electrolyte to the electrodes.

An example of a prior art electrochemical gas sensor is described in U.S. Pat. No. 4,406,770, issued to Chan et al. The sensor includes an electrolyte chamber and a wick that extends from the electrolyte chamber to a separator located between the sensing and counter electrodes. In extending from the chamber to the separator, the wick passes through an opening in a support for the counter electrode. Assembling the sensor thus requires the wick to be threaded through sensor components, thereby increasing the complexity and cost of manufacturing the sensor.

Another example of a prior art electrochemical gas sensor is described in U.S. Pat. No. 5,395,507, issued to Aston et al. The sensor includes a porous, self-supporting body positioned in an electrolyte reservoir for conveying electrolyte to the sensing and counter electrodes. The porous, self-supporting body at least partially supports other components of the sensor, including a separator located between the sensing and counter electrodes.

The sensors described in both of the above patents utilize separate components for the wick and the separator. The use of discrete wick and separator components increases the cost of manufacturing the sensors due to the increased number of parts and the additional labor required to assemble the parts.

A further example of a prior art electrochemical gas sensor is described in U.S. Pat. No. 3,755,125, issued to Shaw et al. The sensor includes absorbent discs that fill the space between and separate the electrodes of the sensor. Some of the discs include an integral wick portion that bends downwardly to extend into a reservoir. The discs are made of any convenient material such as filter paper. The sensor further includes electrically conductive rings for supporting the electrodes.

In view of the characteristics of prior art electrochemical gas sensors, it is an object of the present invention to provide an electrochemical gas sensor which is accurate and sensitive, while also compact, reliable, and relatively simple to manufacture.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention is directed to an electrochemical gas sensor comprising a sensing electrode, a counter electrode, an electrolyte reservoir, an upwardly extending projection disposed within the reservoir that supports the counter electrode, and a wick interposed between, and in contact with, the sensing and counter electrodes. The wick includes an overhang partially disposed in the electrolyte reservoir. The sensor may further include a reference electrode coplanar with and adjacent to the counter electrode.

The shape of the wick allows the wick to both convey the electrolyte from the electrolyte reservoir to the electrodes and maintain the electrolyte between the electrodes. The need for a discrete separator is thus eliminated, reducing the cost of manufacturing the sensor.

The wick may be composed of a material having a density selected to maximize the contact between the electrodes and current collectors that are connected to each of the electrodes. As a result, the contact resistance between the electrodes and the current collectors is reduced, thereby increasing the sensitivity of the sensor.

The placement of the optional reference electrode increases the compactness and sensitivity of the sensor.

Gases that may be detected by the sensor of the present invention include, but are not limited to, carbon monoxide, hydrogen sulfide, chlorine, nitrous oxide, and hydrogen chloride.

BRIEF DESCRIPTION OF THE DRAWINGS

The accompanying drawings, which are incorporated in and constitute a part of the specification, schematically illustrate a preferred embodiment of the invention and, together with the general description given above and the detailed description of the preferred embodiment given below, serve to explain the principles of the invention.

FIG. 1 is a cross-sectional view of the preferred embodiment of the electrochemical gas sensor of the present invention.

FIG. 2 is an exploded view of the preferred embodiment of the electrochemical gas sensor of the present invention.

FIG. 3 is a circuit schematic illustrating the measurement of current from and application of a bias voltage to the preferred embodiment of the electrochemical gas sensor of the present invention.

DESCRIPTION OF THE PREFERRED EMBODIMENT(S)

The present invention will be described in terms of the preferred embodiment. The preferred embodiment of the present invention is shown in FIGS. 1 and 2.

Referring to FIGS. 1 and 2, a sensor 10 includes a sensing electrode 12, a reference electrode 14, and a counter electrode 16. The sensing electrode 12, reference electrode 14, and counter electrode 16 are composed of a polytetrafluorethylene (i.e., Teflon®) substrate coated with a polytetrafluorethylene-bonded platinum black layer (platinum catalyst). These electrodes are electrically conductive and have electrochemically active porous membranes that allow gases to penetrate and react with the platinum catalyst.

Reference electrode 14 and counter electrode 16 are coplanar with and adjacent to each other and are positioned in opposition to sensing electrode 12. This arrangement minimizes the separation between the sensing and counter electrodes since reference electrode 14 is not interposed between the sensing and counter electrodes. The separation between sensing electrode 12 and counter electrode 16 may be, for instance, about 30 mils or less. As a result, the ionic resistance between sensing electrode 12 and counter electrode 16 is minimized, thereby increasing the sensitivity of sensor 10. The reduced separation between the electrodes also minimizes the size of sensor 10.

Reference electrode 14 and counter electrode 16 may be formed on a single substrate by the screen printing process. This process is well-known in the art. Reference electrode 14 and counter electrode 16 are preferably semicircular in shape. Reference electrode 14 and counter electrode 16 may be separated by a spacing of less than, for instance, about 50 mils.

Reference electrode 14 is preferably one-half the surface area of counter electrode 16. This asymmetric sizing of the electrodes has been found to maximize sensor sensitivity while maintaining the correct voltage bias between sensing electrode 12 and reference electrode 14.

The electrochemical reaction involved in the detection of a gas by the present invention will be presented by way of an example. In this example, the gas to be detected is carbon monoxide. At sensing electrode 12 (anode), carbon monoxide is electrochemically oxidized as illustrated by the equation:

$$CO + H_2O = CO_2 + 2H^+ + 2e^-$$

At counter electrode 16 (cathode), a reduction process must take place, such as the reduction of oxygen:

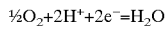

$$\tfrac{1}{2}O_2 + 2H^+ + 2e^- = H_2O$$

The platinum black contained in sensing electrode 12 and counter electrode 16 is a catalyst that promotes the reactions at these electrodes. The overall gas sensor reaction is the sum of these two electrode reactions, namely:

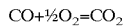

$$CO + \tfrac{1}{2}O_2 = CO_2$$

By Faraday's law, the flux of carbon monoxide reacting at sensing electrode 12 is proportional to the current generated between the two electrodes.

The flux of carbon monoxide to sensing electrode 12 is highly restricted by a diffusion barrier 40 in sensor 10. The diffusion barrier is made of a hydrophobic thin film, such as porous polytetrafluoroethylene. The diffusion barrier thereby enables substantially all the carbon monoxide reaching the sensing electrode to react, thus reducing its concentration at the electrode to essentially zero. The flux of carbon monoxide is therefore determined by the diffusion resistance of the diffusion barrier and the concentration of carbon monoxide external to sensor 10. As a result, the current generated between the two electrodes is directly proportional to the concentration of carbon monoxide external to sensor 10.

Sensor 10 includes current collectors 35, 36, and 37. Current collector 35 is placed between, and is in contact with, sensing electrode 12 and wick 32. Current collector 36 is placed between, and is in contact with, reference electrode 14 and wick 32. Current collector 37 is placed between, and is in contact with, counter electrode 16 and wick 32. The contact between current collectors 35, 36 and 37, and electrodes 12, 14 and 16 create an electrical connection therebetween.

Sensor 10 also includes sensing electrode contact pin 50, reference electrode contact pin 51, and counter electrode contact pin 52. Sensing electrode contact pin 50 contacts current collector 35. Reference electrode contact pin 51 contacts current collector 36. Counter electrode contact pin 52 contacts current collector 37. Contact pins 50, 51, and 52 thereby provide electrical connections to electrodes 12, 14 and 16, respectively, at the external surface of sensor 10.

Sensor 10 further includes locator pin 53, which is used to properly align the sensor with the object to which the sensor is to be secured. The sensor additionally includes signature resistance pins 54 and 55, which present a resistance that, when measured, uniquely identifies the type of sensor, e.g., carbon monoxide sensor, hydrogen sulfide sensor, etc.

Referring to FIG. 3, a sensor system 60 includes sensor 10, a current measuring instrument 20 and a DC voltage source 30. The current generated between sensing and counter electrodes 12 and 16 may be measured by attaching current measuring instrument 20 between sensing electrode contact pin 50 and counter electrode contact pin 52. The current thus measured is an indication of the concentration of the gas, since, as noted, the current generated by sensor 10 is directly proportional to the gas concentration.

Referring back to FIGS. 1 and 2, a bias voltage is maintained between sensing electrode (anode) 12 and reference electrode 14 to avoid generation of undesired currents from reactions involving an oxygen-water redox couple within sensor 10, which would reduce the accuracy of the current measured between sensing electrode 12 and counter electrode 16. The use of a reference electrode and bias voltage is described in further detail in U.S. Pat. No. 3,992,267, issued to Oswin et al.

Referring to FIG. 3 again, the bias voltage may be provided by attaching DC voltage source 30 between sensing electrode contact pin 50 and reference electrode contact pin 51. The bias voltage may be, for instance, 0 volts for sensing carbon monoxide or hydrogen sulfide gas.

Referring back to FIGS. 1 and 2, sensor 10 also includes a housing comprising a top housing portion 18 and a bottom housing portion 20. Sensing electrode 12 is hermetically sealed to, and is thereby supported by, top housing portion 18. The seal is preferably formed by the heat stacking process, which forms a bond by partially melting the parts to be bonded.

Top housing portion 18 includes perforations 42. The perforations permit the gas to be measured to enter sensor 10 and impinge on sensing electrode 12.

Top housing portion 18 also includes aforementioned diffusion barrier 40 and a filter 45. Filter 45 is interposed between diffusion barrier 40 and perforations 42. The filter removes gases that may interfere with the measurement of the gas to be detected. The filter is made of a chemically absorbent material, such as charcoal cloth.

Top housing portion 18 further includes a cap 44. Cap 44 is placed over diffusion barrier 40. The cap secures diffusion barrier 40 and filter 45 within top housing portion 18. The cap has perforations 41 to allow the gas to be measured to enter sensor 10.

Top housing portion 18 additionally includes a top O-ring 46. Top 0-ring 46 is used to provide a seal when coupling sensor 10 to the object within which the gas concentration is to be measured.

Top housing portion 18 is, in turn, sealed to bottom housing portion 20. The sealing may be performed using ultrasonic welding. The bottom housing portion 20 thus supports top housing portion 18. The top and bottom housing portions are made of a nonporous, non-electrically conductive, solid plastic material, such as acrylonitrile-butadiene-styrene (ABS).

Bottom housing portion 20 includes an electrolyte reservoir 26. Electrolyte reservoir 26 is used to store an aqueous electrolyte for use by sensor 10. Since sensor 10 is assembled by the so-called "dry" assembly method, the electrolyte is introduced into reservoir 26 only after the sensor components are assembled. The electrolyte may be, for instance, an aqueous solution of sulfuric acid at a concentration of between 10 and 15 Molar.

Bottom housing portion 20 also includes a combination filling/vent hole 22. Filling/vent hole 22 is used for introducing the electrolyte into electrolyte reservoir 26 after all the sensor components have been assembled. Filling/vent hole 22 is also used for maintaining the pressure in electrolyte reservoir 26 substantially equal to the ambient pressure outside of sensor 10. A membrane 25 covers filling/vent hole 22 to prevent leakage of the electrolyte while equalizing the pressure in the electrolyte reservoir 26. Membrane 25 is made of a hydrophobic, breathable material, such as porous polytetrafluorethylene film. The film may be, for instance, Zitex® G115 film, manufactured by Norton Performance (Wayne, N.J.).

Bottom housing portion 20 further includes side walls 28 and two upwardly extending projections 30. Projections 30 are located in electrolyte reservoir 26 and are made from the same nonporous, solid plastic material as top and bottom housing portions 18 and 20. Reference electrode 14 and counter electrode 16 rest on and are exclusively supported by projections 30.

A wick 32 is partially disposed in electrolyte reservoir 26. Wick 32 includes a disk-shaped body 33 which has a diameter slightly larger than the diameter of sensing electrode 12 so that the disk-shaped body projects slightly beyond the circumferential edges of the sensing, reference, and counter electrodes. A flange 34 projects downwardly from the outer edge of disk-shaped body 33, forming a recess 38. When sensor 10 is assembled, disk-shaped body 33 is interposed between, and in contact with, sensing electrode 12 and coplanar reference and counter electrodes 14 and 16. Flange 34 circumferentially surrounds and projects below the coplanar reference and counter electrodes 14 and 16 into reservoir 26. Wick 32 thereby transports electrolyte from reservoir 26 to the area in which the electrochemical reaction occurs, i.e., between sensing electrode 12 and coplanar reference and counter electrodes 14 and 16.

Wick 32 does not perform a supporting function for a separator, which is not present, or any other component of sensor 10. As noted earlier, sensing electrode 12 is supported by top housing portion 18, and reference and counter electrodes 14 and 16 are supported by projections 30.

The shape of wick 32 simplifies the assembly of sensor 10. Since the wick circumferentially surrounds reference and counter electrodes 14 and 16, the wick does not need to be threaded through the electrodes, thus simplifying the assembly process. Since the wick is constructed in a single piece that extends between sensing electrode 12, and coplanar reference and counter electrodes 14 and 16, no separators are required or used in sensor 10, thus further simplifying the assembly process.

Wick 32 is made of a hydrophilic material, such as glass fiber or surface-treated porous, polypropylene or polyethylene sponge. A hydrophilic material is used for the wick to retain and immobilize the electrolyte, thereby ensuring that an adequate amount of electrolyte wets the surfaces of the electrodes. As a consequence, the equilibrium between the electrodes and the electrolyte is maintained even under changing orientations of sensor 10.

When sensor 10 is assembled by coupling top and bottom housing portions 18 and 20, electrodes 12, 14 and 16, and current collectors 35, 36 and 37 are pressed into contact with each other, thereby forming an electrical connection. The density of wick 32, combined with the support of coplanar reference and counter electrodes 14 and 16 by projections 30, ensures that a firm electrical contact is developed.

The wick 32 is constructed of a material whose density is selected to maximize the electrical contact between electrodes 12, 14 and 16, and current collectors 35, 36 and 37. The wick thereby minimizes the contact resistance between the electrodes and the current collectors, increasing the sensitivity of sensor 10. The density of the material used to construct the wick may be between about 0.05 and 0.85 grams per cubic centimeter ($g/cm^3$), and more preferably between 0.2 and 0.6 $g/cm^3$. For instance, the wick may be constructed of a custom-manufactured polypropylene material made by Pore Technology (Framingham, Mass.). The material is surface treated to provide it with hydrophilic characteristics. This material has a pore size of about 100 microns, a density of about 0.4 $g/cm^3$, and a porosity of about 60%.

Sensor 10 achieves a relatively high sensitivity due to the use of the features specified above. The sensitivity of sensor 10 has been measured at a value of about 0.1 microamperes per parts per million ($\mu A/ppm$).

In summary, an apparatus for detecting and measuring a gas has been described. The apparatus as described in the preferred embodiment includes a wick comprised of a material that maximizes the electrical contact between the electrodes and the current collectors and formed in a shape that facilitates sensor assembly. The apparatus optionally further includes a reference electrode that is positioned coplanar with and adjacent to the counter electrode such that the compactness and sensitivity of the sensor is maximized.

The present invention has been described in terms of a preferred embodiment. The invention, however, is not limited to the embodiment depicted and described. Rather, the scope of the invention is defined by the appended claims.

What is claimed is:

1. An electrochemical gas sensor comprising:
   a top housing portion;
   a bottom housing portion;
   a sensing electrode supported by said top housing portion;
   a counter electrode;
   a reservoir for storing an electrolyte;
   at least one upwardly extending projection of said bottom housing portion that supports said counter electrode; and
   a wick interposed between said sensing electrode and said counter electrode, said wick including a disk portion having a diameter larger than the diameter of said counter electrode such that the disk portion extends beyond a circumferential edge of said counter electrode with an overhang portion of said wick extending from said disk portion into said reservoir.

2. The electrochemical gas sensor of claim 1, wherein said overhang portion circumferentially surrounds said counter electrode.

3. The electrochemical gas sensor of claim 1 further comprising:
   a first current collector disposed between said sensing electrode and said wick;
   a second current collector disposed between said counter electrode and said wick; and
   wherein said wick has a density that substantially maximizes the electrical contact between said sensing electrode and said first current collector and between said counter electrode and said second current collector.

4. The electrochemical gas sensor of claim 1, wherein said wick has a density of between approximately 0.05 grams per cubic centimeter and approximately 0.85 grams per cubic centimeter.

5. The electrochemical gas sensor of claim 1 further comprising a reference electrode coplanar with and adjacent to said counter electrode.

6. The electrochemical gas sensor of claim 5, wherein a surface area of said reference electrode is approximately one-half that of said counter electrode.

7. The electrochemical gas sensor of claim 1 further comprising a sensor housing including a top housing portion and a bottom housing portion, said top housing portion supporting said sensing electrode and said bottom housing portion including said reservoir and said at least one upwardly extending projection.

8. The electrochemical gas sensor of claim 7, wherein said sensing electrode is hermetically sealed to said top housing portion by a heat stacking process.

9. The electrochemical gas sensor of claim 7, wherein said bottom housing portion includes a hole for filling said reservoir with said electrolyte and for maintaining said reservoir at a pressure substantially equal to an ambient pressure, wherein said hole is covered by a membrane made of a hydrophobic, breathable material.

10. An electrochemical gas sensor comprising:
    a sensing electrode;
    a counter electrode;
    a reservoir for storing an electrolyte;
    at least one upwardly extending projection disposed within said reservoir that supports said counter electrode;
    a wick interposed between, and in contact with, said sensing electrode and said counter electrode, said wick including a disk portion and a flange portion projecting from an edge of said disk portion to form a recess, said flange portion partially disposed in said reservoir; and
    wherein said counter electrode and a portion of said at least one upwardly extending projection are disposed within said recess of said wick.

11. The electrochemical gas sensor of claim 10 further comprising:
    a first current collector disposed between said sensing electrode and said wick;
    a second current collector disposed between said counter electrode and said wick; and
    wherein said wick has a density that substantially maximizes the electrical contact between said sensing electrode and said first current collector and between said counter electrode and said second current collector.

12. The electrochemical gas sensor of claim 10, wherein said wick has a density of between approximately 0.05 grams per cubic centimeter and approximately 0.85 grams per cubic centimeter.

13. The electrochemical gas sensor of claim 10 further comprising a reference electrode coplanar with and adjacent to said counter electrode.

14. The electrochemical gas sensor of claim 13, wherein a surface area of said reference electrode is approximately one-half that of said counter electrode.

15. The electrochemical gas sensor of claim 10 further comprising a sensor housing including a top housing portion and a bottom housing portion, said top housing portion supporting said sensing electrode and said bottom housing portion including said reservoir and said at least one upwardly extending projection.

16. The electrochemical gas sensor of claim 15, wherein said sensing electrode is hermetically sealed to said top housing portion by a heat stacking process.

17. The electrochemical gas sensor of claim 15, wherein said bottom housing portion includes a hole for filling said reservoir with said electrolyte and for maintaining said reservoir at a pressure substantially equal to an ambient pressure, wherein said hole is covered by a membrane made of a hydrophobic, breathable material.

18. An electrochemical gas sensor comprising:
    a sensing electrode;
    a top housing portion supporting said sensing electrode;
    a counter electrode;
    a reference electrode coplanar with, and adjacent to, said counter electrode, said reference electrode having a surface area unequal to the surface area of said counter electrode;
    a bottom housing portion including at least one upwardly extending projection supporting said counter and reference electrodes and a reservoir for storing an electrolyte;
    a wick interposed between, and in contact with, said sensing electrode and said counter electrode, said wick including a disk portion and a flange portion projecting from an edge of said disk portion to form a recess, said flange portion partially disposed in said reservoir;
    a first current collector disposed between said sensing electrode and said wick;
    a second current collector disposed between said counter electrode and said wick; and
    wherein said counter and reference electrodes and a portion of said at least one upwardly extending projection are disposed within said recess of said wick and said wick has a density that substantially maximizes the electrical contact between said sensing electrode and said first current collector and between said counter electrode and said second current collector.

19. The electrochemical gas sensor of claim 18, wherein said density of said wick is between approximately 0.05 grams per cubic centimeter and approximately 0.85 grams per cubic centimeter.

20. The electrochemical gas sensor of claim 18, wherein a surface area of said reference electrode is approximately one-half that of said counter electrode.

21. The electrochemical gas sensor of claim 18, wherein said sensing electrode is hermetically sealed to said top housing portion by a heat stacking process.

22. The electrochemical gas sensor of claim 18, wherein said bottom housing portion includes a hole for filling said reservoir with said electrolyte and for maintaining said reservoir at a pressure substantially equal to an ambient pressure, wherein said hole is covered by a membrane made of a hydrophobic, breathable material.

* * * * *